United States Patent
Rosenberg et al.

(10) Patent No.: US 7,238,370 B2
(45) Date of Patent: Jul. 3, 2007

(54) METHOD AND COMPOSITION TO PREVENT AND TREAT PHOTOAGING OF SKIN

(76) Inventors: E. William Rosenberg, 6055 Sweetbriar Cove, Memphis, TN (US) 38120; Robert B. Skinner, 349 Riverbluff Pl., Memphis, TN (US) 38103; George Flinn, Jr., 188 S. Bellvue Blvd., Memphis, TN (US) 38104

( * ) Notice: Subject to any disclaimer, the term of this patent is extended or adjusted under 35 U.S.C. 154(b) by 481 days.

(21) Appl. No.: 10/268,801

(22) Filed: Oct. 11, 2002

(65) Prior Publication Data

US 2003/0232062 A1 Dec. 18, 2003

(51) Int. Cl.
  *A61K 9/14* (2006.01)
  *A61K 9/00* (2006.01)
(52) U.S. Cl. ............................. 424/489; 424/400
(58) Field of Classification Search ............. 424/400, 424/489
  See application file for complete search history.

(56) References Cited

U.S. PATENT DOCUMENTS

| | | | |
|---|---|---|---|
| 3,092,111 A | | 6/1963 | Saperstein et al. |
| 3,944,506 A | * | 3/1976 | Hramchenko et al. |
| 4,048,123 A | | 9/1977 | Hramchenko et al. |
| 4,957,747 A | * | 9/1990 | Stiefel |
| 5,380,359 A | * | 1/1995 | Honda et al. |
| 5,441,666 A | | 8/1995 | Dotolo |
| 5,523,014 A | * | 6/1996 | Dolan et al. |
| 5,720,963 A | | 2/1998 | Smith |
| 5,910,476 A | | 6/1999 | Kinsman et al. |
| 6,634,576 B2 | * | 10/2003 | Verhoff et al. |
| 6,673,756 B2 | * | 1/2004 | Sonnenberg et al. |
| 6,703,004 B2 | * | 3/2004 | Narasimhan et al. |
| 6,712,617 B2 | * | 3/2004 | Detmar et al. |

OTHER PUBLICATIONS

*The Effects Of An Abrasive Agent On Normal Skin and On Photographed Skin In Comparison With Topical Tretinoin*; R. Marks, et al.; Br J Dermatol Oct. 1990; 123(4); 457-66 (Abstract only).

The Next "Hot" Cosmetic Procedure, Skin & Aging, Oct. 2004, p. 34.

Elias, PM., et al., Interactions Among Stratum Corneum Defensive Functions, Blackwell Munksgaard Experimental Dermatology 2005, 14: 719-726.

Harder, J., et al., Differential Gene Induction of Human β-Defensins (hBD-1, -2, -3 and -4) in Keratinocytes is Inhibited by Retinoic Acid, Journal of Investigative Dermatology, vol. 123, Issue 3, p. 522, Sep. 2004.

(Continued)

*Primary Examiner*—Humera N. Sheikh
(74) *Attorney, Agent, or Firm*—Connolly Bove Lodge & Hutz LLP

(57) ABSTRACT

A method and composition for stimulating skin function to prevent and reverse the effects of photoaging, without removal of the protective stratum corneum. The composition of the invention is a mixture of coarse pumice and an aqueous surfactant emulsion.

9 Claims, 1 Drawing Sheet

OTHER PUBLICATIONS

Ong, P., et al., Endogenous Antimicrobial Peptides and Skin Infections in Atopic Dermatitis, N Engl J Med, Oct. 10, 2002, vol. 347, No. 15, p. 1151-1160.

Nomura, I., et al., Cytokine Milieu of Atopic Dermatitis, as Compared to Psoriasis, Skin Prevents Induction of Innate Immune Response Genes, The Journal of Immunology, 2003, 171:3262-3269.

Fisher, AA et al, Arch Dermatol., Persulfate hair bleach reactions. Cutaneous and respiratory manifestations, Oct. 1976; 112(10): 1407-9.

Section—5: Hardners/Emery Abrasive Aggregates, Anti-Hydro International, Inc. Oct. 28, 2005.

* cited by examiner

METHOD AND COMPOSITION TO PREVENT AND TREAT PHOTOAGING OF SKIN

FIELD OF THE INVENTION

The present invention relates generally to a method and composition for improving photoaged skin. More specifically, the invention relates to use of a granular composition for stimulation of skin revitalization.

BACKGROUND OF THE INVENTION

Human skin is composed of several layers, which include the dermis, epidermis, and stratum corneum. See MacKie, R. M., *Clinical Dermatology* (1996). The dermis has many elements, including vascular components which supply nutrients, fat cells which serve as energy depots and metabolic regulators, nerve cells, and elastic fibers. The epidermis lies exterior to the dermis and is composed of keratinocytes that produce growth factors important in the regulation of skin cell replication. The stratum corneum is the outermost barrier layer and is composed of cornified epidermal cells. The stratum corneum provides a barrier to loss of moisture and to environmental insults.

Skin is damaged by exposure to a variety of environmental factors, including ultraviolet light from sunlight or intentional tanning lights, and by tobacco smoke inhalation. Damage to skin is exacerbated by aging, and the combination effect is known as photoaging. Photoaging of skin results in thinning of the dermis, formation of the wrinkles, loss of skin elasticity, loss of natural oils, dryness, scaling, and irregular pigmentation. In the process of photoaging the collagen and elastin fibers of the dermis degrade and weaken, contributing to a thinning of the skin. In addition, microdeposits of fat are sometimes diminished in the skin. The muscle layers underlying the skin can also relax to contribute to a loose skin appearance. Conversely, some specific muscles associated with the skin can contract to cause frown lines, laugh lines, and other wrinkles or skin creases The wide variety of treatments for photoaged skin and wrinkles may reflect, in part, the relative inefficacy of the treatments, the lack of control of the treatment by the individual, or the potentially adverse side effects of known treatments. Representative known skin treatments are discussed below.

A wide variety of chemical treatments have been used to resurface the skin Deep and mid-level treatments have used organic chemicals such as phenol or trichloroacetic acid. Undesirable after-effects from these treatments can include swelling, oozing, blistering, and pain More superficial chemical exfoliative treatments, or "peels," include treatments with alpha hydroxy glycolic, lactic, or other acids, are used to remove skin layers, and have been used in combination with abrasive treatments. By thinning the stratum corneum, alpha hydroxy acids increase the sensitivity of the skin to sunlight. Some reports also suggest that they increase long term production of wrinkles. More fundamentally, such treatments render the patient more susceptible to the deleterious effects of ultraviolet radiation.

Topical treatment with retinoic acid (Retin A) is another common skin treatment and is widely used for acne treatment. Retinoic acid affects cell function and results in a loosening of the cells at the surface of the skin. Serious concerns exist, however, regarding whether retinoic acid treatment may play a role in the development of skin cancers. In an experimental model, topical application of retinoic acid augmented photocarcinogenesis by reducing the latency period, increasing the total numbers of tumors, and decreasing survival time. Halliday, G. M. et al., *Topical retinoic acid enhances, and a dark tan protects, from subedemal solar-simulated photocarcinogenesis*. 114 J. Invest. Dermatol. 923 (2000).

Abrasion techniques with wire brushes, diamond grinding wheels, microderm abrasion, or more recently, with laser ablation, are also used to smooth wrinkles and skin scars. Another abrasion method involves abrasion of the stratum corneum with aluminum oxide abrasives, e.g. Brasivol®. Marks, R. *The effects of an abrasive agent on normal skin and on photoaged skin in comparison with topical tretinoin*, 123 Br. J. Dermatol. 457 (1990). In this method, the desquamation (i.e. stripping) of the stratum corneum is increased. Moreover, several changes in the skin were noted: the epidermal labeling index, i.e., the replication of keratinocytes, was increased, the cutaneous blood flow was increased, the force necessary for skin extensibility was increased, and skin thickness was increased. However, increased desquamation is also associated with increased sensitivity to sunlight and thereby to photodamage of the skin, including wrinkling and dryness, and to an increased risk of neoplasia. Moreover, the method is reported to lead to minor dermatitis that can require use of hydrocortisone. U.S. Pat. No. 4,957,747

Abrasive skin cleaners are old in the art. The manufacture of Lava brand soap was begun in the nineteenth century. U.S. Pat. No. 5,910,476 to Kinsman, et al. discloses a soap bar having pumice or other abrasive. U.S. Pat. No. 5,441,666 to Dotolo discloses an abrasive hand cleaner having D-limonene and from about 2.5 to about 11 percent pumice by weight. U.S. Pat. No. 3,092,111 to Saperstein, et al. describes a composition and method using aluminum oxide for the therapeutic abrasion of human skin for the treatment of acne to induce desquamation.

Various treatments of aged skin have been proposed. The U.S. Pat. No. 4,957,747 to Stiefel describes a method for improvement of firmness and tone of aged skin by repeated desquamation using a suspension of fine aluminum oxide abrasive. The U.S. Pat. No. 5,720,963 to Smith discloses use of cerebrosides, which are biological regulators, to inhibit the repair of a disrupted skin moisture barrier.

Surgical techniques have also been used to improve skin appearance. Among these are facial reconstructions, including "face lifts," which are used for more general aesthetic effects, and surgically remove the slack in loose, inelastic skin.

What has not been available is a way of stimulating renewal of the skin without topical biological regulators, desquamating abrasives, or exfoliating chemicals.

SUMMARY OF THE INVENTION

The present invention is directed to a method of preventing, ameliorating, or reversing skin photoaging comprising topically applying a granular composition to an exterior surface of the skin comprising a stratum corneum. The granular composition useful in the method of the invention can comprise coarse, water-insoluble particles as a suspension or paste in an aqueous emulsion. In one embodiment the particles comprise between about 12% (by weight, w/w) and about 30% (w/w) of the composition. A variety of particles that are not too hard are useful in the granular composition of the invention. In one preferred aspect, the particles can be pumice. In one aspect of the invention, the topical application of a granular composition comprises rolling the granular composition on the surface of the skin with at least one of a generally circular, longitudinal and reciprocating motion. The stratum corneum is not abraded from the surface of the skin, although micropuncturing of the skin or stratum corneum is contemplated. The application of the granular composition can be made at least about daily. In one aspect, the particles of the granular composition are characterized by a hardness measured on the Moh scale of between about three and seven, preferably between about four and about six, and most preferably about six, or its equivalent. In one aspect, the coarseness of the pumice is characterized as having a grade of number 3, corresponding to particles having an average size of about 0.3 mm in size. Particles having greater coarseness, e.g. about 0.8 mm, are also suitable. The granular composition is advantageously applied to the facial skin. In another embodiment, the granular composition is advantageously applied to the hand skin. In yet a further embodiment the granular composition is advantageously applied to skin of the shoulder, chest, back, scalp, and/or arm. In another embodiment of the method of the invention, the granular composition further comprises between about 2% (w/w) and about 8% (w/w) of at least one wax.

In one aspect, the invention comprises a granular composition for use to prevent, ameliorate, or reverse skin photoaging comprising between about 12% (w/w) and about 30% (w/w) coarse pumice. In a preferred embodiment, the granular composition comprises an aqueous emulsion. In a more preferred aspect, the granular composition comprises between about 5% (w/w) and about 23% (w/w) of at least one surfactant. In a yet more preferred aspect, the granular composition comprises between about 2% (w/w) and about 8% (w/w) of at least one wax. In a still more preferred aspect, the granular composition comprises between about 35% (w/w) and about 80% (w/w) water and may preferably comprise at least one surfactant and at least one wax. In one aspect, the granular composition of the invention provides a surfactant that is not a soap, where a soap is an alkali metal or ammonium salt of a fatty acid. In another embodiment of the granular composition of the invention, the granular composition further comprises about 1% (w/w) silicone. In another aspect the granular composition of the invention comprises a surfactant where the surfactant is selected from the group consisting of a sulfated alkyl alcohol, a polyethylene glycol bisalkylate, a polyethylene glycol bisalkenylate, a polyoxyethylenated alkyl alcohol, a polyoxyethylene (20) sorbitan monoalkylate, a polyoxyethylene (20) sorbitan monoalkenylate, an alkylbenzene sulfonate, or mixture thereof, with the proviso that the alkyl alkenylate, and alkylate moieties each consist of 8-24 carbon atoms.

In another aspect, the invention provides a kit for use to prevent, ameliorate, or reverse the effects of skin photoaging, comprising (a) a granular composition comprising between about 12% (w/w) and about 30% (w/w) coarse pumice in an aqueous emulsion, and (b) at least one of a package label and a package insert comprising instructions for the use of said granular composition to prevent, ameliorate, or reverse skin photoaging. In one embodiment of the kit, the granular composition further comprises at least one of at least one surfactant. In a preferred embodiment of the kit, the granular composition further comprises between about 2% (w/w) and about 11% (w/w) of at least one wax. In a preferred embodiment of the kit, the pumice is characterized as having a grade of number 3.

BRIEF DESCRIPTION OF THE DRAWING

The figure illustrates photomicrographs of guinea pig skin. The dorsal hair of guinea pigs was shaved and the skin was treated daily with the granular composition of the invention, left untreated, or treated with Retin A, 0.1% (w/v). After one month skin biopsies were prepared, fixed, sectioned, and stained.

DETAILED DESCRIPTION OF THE INVENTION

Figure 1A:
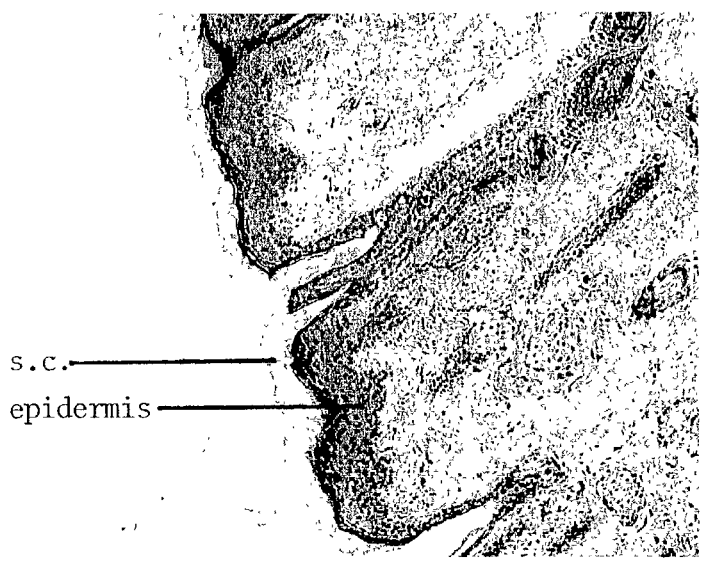
FIG. 1A is a photomicrograph of skin from an animal treated with the granular composition of the invention, 100×.

The method of the invention provides a method for improving long term skin function and appearance. The method can be used to prevent or substantially prevent the photoaging of skin, to ameliorate the effects and signs of photoaging, and/or to reverse or partially reverse the ravages of photoaging. Without being limited to a specific mechanism of action, rolling the granular composition of the invention on the skin can produce a plurality of small holes in the stratum corneum. The stratum corneum of human skin has many layers of cornified cells and the holes are thought to extend through some or all of the layers of the stratum corneum. The cells of the stratum corneum are keratinized and non-nucleated. Some of the holes may expose the underlying cells of the vital epithelium. The process of microperforation can stimulate the cells of the skin, that is, the keratinocytes of the epidermis can be stimulated to replicate by use of the method of the invention. The dermis can also be stimulated by the method of the invention. The thickness, cellularity, and resiliency of the dermis can be improved upon using the granular composition, and fine wrinkles are diminished or disappear. The instant invention may also manipulate, massage, and exercise the skin to induce and encourage improved function. By contrast oil-based creams and lotions that temporarily increase the barrier functions of the skin by coating the skin with excess mineral or biological oil are believed to inhibit cell replicative function. It may be that the presence of an intact stratum corneum, whether enhanced with excess oils or not, prevents the access of environmental or hormonal cues to the viable cells of the epidermis and dermis. The composition of the invention can be applied to the skin by using any suitable means, including fingers, hands and washcloth. Preferably, fingertips are used to apply the composition.

One advantage of the instant invention is that the stratum corneum is largely left intact, so that the stratum corneum can function as a barrier to ultraviolet radiation. Exposure of the skin over long periods to sunlight and the ultraviolet light that it contains can increase the risk of skin cancers and contribute to the deterioration of skin structure. Chemical or physical treatments that remove the stratum corneum, such as alpha hydroxy acids, retinoic acid, or harsh abrasives (e.g. aluminum oxide), are known to increase sensitivity of the skin to ultraviolet radiation and may put individuals using such products at increased risk of skin cancer. By contrast, the method of the instant invention substantially retains the stratum corneum layer of the skin to block or attenuate ultraviolet radiation. Still another advantage is the ability to use the compositions near sensitive body areas, such as the eyes. Moreover, as the stratum corneum is retained, the method of the invention is not associated with the bleeding or oozing characteristic of some skin treatments. In one aspect of the invention, greater than about 50% of the stratum corneum is left intact. In a more preferred aspect of the invention, greater than about 90% of the stratum corneum is left intact. In a most preferred aspect of the invention, essentially 100% of the stratum corneum is left intact.

The instant invention provides a composition useful to prevent, ameliorate, or reverse skin photoaging. The granular composition comprises coarse, water-insoluble particles, including, but not limited to, between about 12% (w/w) and about 30% (w/w) of coarse, water-insoluble particles. Any coarse or granular particle is suitable for use in the invention, with the proviso that the particle should not be too hard an abrasive. Suitable particles useful in the invention are essentially water-insoluble and include, but are not limited to: pumice, granulated feldspar, perlite, silica sand, olivine sand, ceramic beads, glass beads, granulated oyster shells, granulated walnut shells, and granulated apricot pits, or combinations thereof. A suitable particle is coarse pumice. Pumice is a frothy volcanic glass or rock, e.g. feldspar, with a typical composition of about 70% silica, about 13% aluminum oxide, and lesser amounts of iron, potassium, and sodium oxides. In a preferred embodiment, the composition comprises between about 15% (w/w) and about 25% (w/w) coarse pumice. In an even more preferred embodiment, the granular composition comprises about 20% (w/w) coarse pumice. The particle is characterized by a hardness on the Moh scale of less than about 7. In one embodiment, a suitable particle can have a hardness of between about 5.5 and about 6.5 on the Moh scale, but softer and somewhat harder particles are also suitable. A hard abrasive, e.g., substantially pure aluminum oxide which has a hardness of 8-9 on the Moh scale, is not useable in the methods and compositions of the invention. Furthermore, in one aspect, the particles are sharp-edged and capable of microperforation of the stratum corneum and/or the skin. In one embodiment, the coarseness of the pumice is properly characterized as having a grade of number 3. Coarse pumice has individual grains of about 0.3 mm in the longest axis, and can include particles that are somewhat smaller and larger in size. Abrasive skin cleaners such as Lava soap have pumice that is less coarse. The smaller, less coarse particles in abrasive cleaners get underneath the soil to help scrub away soil and grime. Moreover, use of such abrasive cleaners can remove stratum corneum. Unlike abrasive cleaners and abrasive scrubbers, the nonabrasive composition of the instant invention is designed to not abrade the stratum corneum. Moreover, the composition of the instant invention is useful to stimulate the skin rather than clean the skin.

The granular composition of the invention can optionally further include an aqueous emulsion having between about 35% (w/w) and about 80% (w/w) of water. In a preferred embodiment, the granular composition comprises between about 50% (w/w) and about 60% (w/w) of water. Any form of water is suitable for the invention including deionized, distilled, filtered, purified, and tap water.

In one aspect, the aqueous emulsion comprises between about 5% (w/w) and about 35% (w/w) of at least one surfactant. In a preferred embodiment, the aqueous emulsion comprises between about 5% (w/w) and about 23% (w/w) of at least one surfactant. In one embodiment, the emulsion comprises between about 15% (w/w) and about 23% (w/w) of at least one surfactant. Moreover, the emulsion can be about 16%, about 18%, about 20%, about 24%, or about 26% surfactants. In a more preferred embodiment, the emulsion is about 22% (w/w) of at least one surfactant. Any of a number of surfactants are suitable for use in the composition and methods of the invention. Without limiting to specific surfactants, the surfactant can include a sulfated alkyl alcohol, a polyethylene glycol bisalkylate, a polyethylene glycol bisalkenylate, a polyoxyethylenated alkyl alcohol, a polyoxyethylene sorbitan monoalkylate, an alkyl sulfonate, an olefin sulfonate, an alkyl ethoxylate, a polyoxyethylene sorbitan monoalkenylate, and an alkylbenzenesulfonate. Moreover, a mixture of surfactants can be advantageously used. In the description of surfactants, it is understood that alkyl, alkenylate, and alkylate each refer to moieties consisting of 8-24 carbon atoms. In a preferred embodiment, alkyl, alkenylate, and alkylate each refer to moieties consisting of 10-18 carbon atoms. As an example, the surfactant can be, but is not limited to, the sulfated alkyl alcohol termed sodium dodecyl sulfate. As another example, the sulfated alkyl alcohol can be lithium tetradecyl sulfate. As yet another example, the polyoxyethylene sorbitan monoalkylate can be, but is not limited to polyoxyethylene (20) sorbitan laurate, sometimes known in the trade as polysorbate 20. As yet another example, polyoxyethylene sorbitan monoalkenylate can be polyoxyethylene (20) sorbitan monooleate, also known as polysorbate 80.

In one aspect, the aqueous emulsion comprises between about 2% (w/w) and about 11% (w/w) of at least one wax, preferably between about 2% (w/w) and about 8% (w/w). In one preferred embodiment, the aqueous emulsion comprises between about 4% (w/w) and about 7% (w/w) wax or waxes. In one preferred embodiment, the granular composition comprises about 5% (w/w) wax. Any of a number of types of natural or synthetic waxes may be included in the composition of the invention, including beeswax, orange peel wax, cera bellina, jasmine, candelilla, siliconyl beeswax, siliconyl candelilla, kester beads, shea butter, ceresine, paraffin, carnauba, n-tetradecanol, i-tetradecanol, n-pentadecanol, i-pentadecanol, n-hexadecanol, i-hexadecanol, n-heptadecanol, i-heptadecanol, n-octadecanol, and i-octadecanol. In one preferred embodiment the wax comprises cetyl alcohol. A wax having a melting temperature generally similar to skin temperature is advantageous.

Any preservative known to one of skill in the art of formulary can be used in the granular composition of the invention, including, but not limited to Germaben II (about 1%) and benzyl alcohol (about 0.5%).

The granular composition of the invention can optionally comprise added colorants and/or perfumes, as known to one skilled in the art. In one embodiment, the granular composition has no added colorants or perfumes.

The table provides a preferred embodiment of the composition of the invention, and method of preparation of the composition. The components listed (as w/w) in part A of the table are heated to 180° F. Substantially simultaneously, the components listed in part B of the table are also heated to 180° F. Then parts A and B are mixed rapidly for about 15 minutes. The mixture is cooled to 145° F. and the components of part C are added and further mixed. During this step the temperature is not allowed to fall below 140° F. After thorough mixing, the mixture is cooled to 120-130° F. and suitable containers are filled.

In one aspect of the invention the granular composition does specifically comprise less than 30%, preferably less than 10%, and most preferably about 0% (w/w) of a soap. A soap is the reaction product of a fatty acid and an alkali or carbonate. In one aspect of the invention, the granular composition does not comprise limonene. In one aspect of the invention, the granular composition does not comprise a hydrocarbon oil. In one aspect of the invention, the granular composition does not comprise a hydrocarbon solvent. In one aspect of the invention, the granular composition does not comprise sodium hydroxide. In one aspect of the invention, the granular composition does not comprise citrate. In one aspect, the granular composition does not comprise a hydroxyl carboxylic acid. In one aspect the granular composition does not comprise a cerebroside. In one aspect the granular composition comprises less than 15%, preferably about 0% (w/w) of borate. In one aspect of the invention, the granular composition comprises at least one of a soap, limonene, a hydrocarbon oil, a hydrocarbon solvent, sodium hydroxide, citrate, a hydroxyl carboxylic acid, a cerebroside, and borate.

In one embodiment of the invention, the granular composition comprises about 1% (w/w) silicone.

TABLE 1

Facial Treatment Formula

| PART A | |
|---|---|
| Purified Water | 56.90 |
| Sodium lauryl sulfate | 6.60 |
| Polysorbate 20 | 2.00 |
| Benzyl alcohol | 0.50 |
| PART B | |
| Glyceryl monostearate, self-emulsifying | 6.00 |
| Cetyl Alcohol | 5.00 |
| Polysorbate 20 | 2.00 |
| Dow Corning Silicone 200/350 | 1.00 |
| PART C | |
| Pumice No. 3 | 20.00 |
| | 100.00 |

Suitable sources for the materials of the granular composition are sodium lauryl sulfate, Chemron, Bowling Green, Ohio; polysorbate 20, glyceryl monostearate, and cetyl alcohol, Jeen International Corp., Fairfield, N.J.; benzyl alcohol, Ideal Chemical; dimethyl silicone, Lambent Technologies, Norcross, Ga.; and pumice, CR Minerals, Boulder, Colo.

Several grades of granular particle are suitable for use in the invention. Without being limited to a specific material, one granular particle which is suitable is grade 3 pumice. Grade 3 pumice has a typical particle size and size distribution analysis as disclosed in Table 2:

TABLE 2

Pumice Particle Sizes

| Particle size, microns | Composition, % by weight, of Grade 3 pumice | Composition, % by weight, of Grade 4 pumice |
|---|---|---|
| 1410 | | 1–40 |
| 840 | | 25–55 |
| 595 | <5 | 5–30 |
| 420 | 20–40 | 5–30 |
| 297 | 40–60 | 1–20 |
| 250 | 10–30 | <5 |
| 177 | <10 | |
| 149 | <5 | |

In one aspect, the invention provides a kit for use to prevent, ameliorate, or reverse skin photoaging. In addition to a container comprising a granular composition, the kit comprises a label, a package insert, or both, having instructions for use, contraindications, warnings and/or expected results, related to skin photoaging. The granular composition comprises between about 12% (w/w) and about 30% (w/w) of coarse particles that can include pumice.

EXAMPLES

Example 1

The granular composition of the invention was daily applied topically to only one hand of an individual using a gentle rolling action. After several months of routine application, the skin of the hand receiving the treatment was more youthful in appearance. Sonigraphic measurement of the skin revealed that the skin of the treated hand is thicker than that of the untreated hand. As skin thickness decreases from infants to the elderly, the increased skin thickness is consistent with a better and more youthful appearance.

Example 2

Nine guinea pigs were treated as follows. The dorsal hair was shaved bilaterally and daily. The left and the right side of each guinea pig were treated with one of (1) the granular composition of the invention, applied daily for about one minute, five days per week, for one month, (2) Retin A, 0.1%, applied topically daily, five days per week, for one month, or (3) control, no further treatment. After one month, skin biopsies were evaluated by a veterinary pathologist blind to the treatment of individual samples.

Figure 1B:
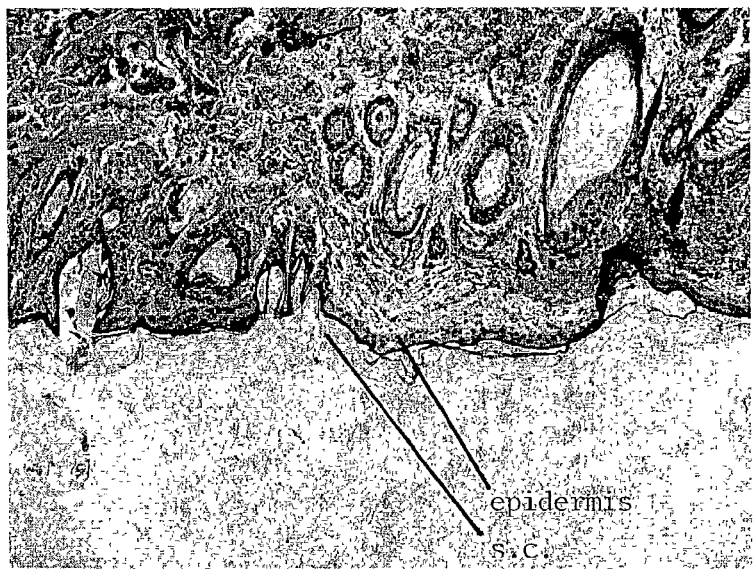
FIG. 1B is a photomicrograph of skin from an untreated animal, 100×.
Figure 1C:
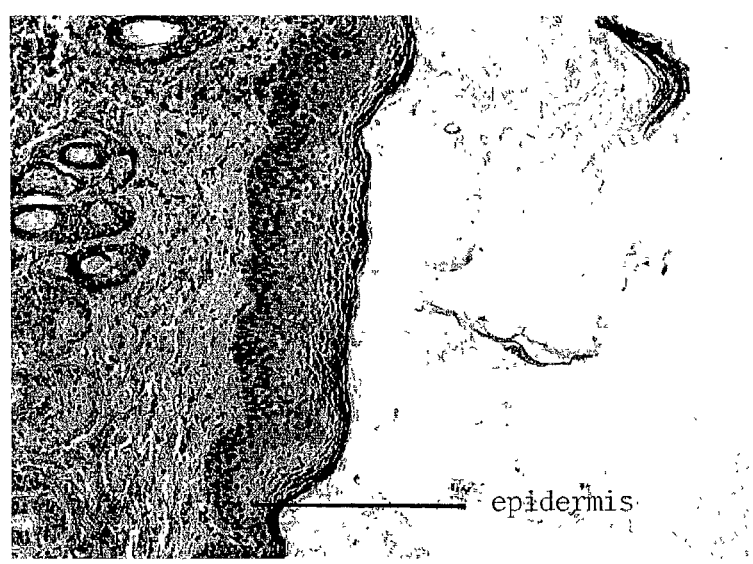
FIG. 1C is a photograph of skin from an animal treated with Retin A, 400×.

The total skin thickness was increased by treatment with either the granular composition of the invention, FIG. 1A; compared to control, FIG. 1B; or by Retin A, FIG. 1C.

The photographs demonstrate at least two benefits of the product of the invention. One, use of the product of the invention led to a thicker epidermis that was very cellular when compared to the control. Two, in contrast to the treatment with Retin A, which strips the stratum corneum, the stratum corneum (s.c.) was substantially unaffected by treatment with the granular composition of the invention. That is, desquamation was minimal with application of the granular composition. The photographs clearly indicate that the granular composition of the instant invention does not abrade the skin, but rather, leaves the stratum corneum intact.

Example 3

The composition of the invention is applied to the facial skin of an individual for seven days at a frequency of once per day. The granular composition is gently rolled onto the skin using a circular motion for about 30 seconds. The composition of the invention is subsequently rinsed off with flowing water. At the end of seven days, the skin is found to be slightly smoother, slightly shinier, and slightly more uniform. The individual is advised to use the treatment indefinitely and for at least six weeks.

Example 4

The granular composition of the invention is applied to the scalp skin and hair of an individual for seven days at a frequency of once per day. The granular composition is gently rolled onto the scalp skin and through the hair, using a combination of a circular motion and a reciprocating motion for about 2 minutes. The granular composition of the invention is subsequently easily rinsed off with flowing water. At the end of seven days, the scalp skin is found to be slightly smoother and somewhat more uniform, and the hair is soft and manageable. The individual is advised to use the treatment daily and indefinitely Example 5

The granular composition of the invention is applied to the skin of the hands of yet another individual twice each day. The granular composition is gently rolled onto the skin with the fingers and palm of the opposite hand, using a combination of a circular motion and a longitudinal motion for about 1 minute per hand. The granular composition of the invention is removed with a wet towel. With continued use, the skin of the hands is found to be less rough and more supple.

Example 6

The granular composition is prepared to consist of, by weight, 18% no. 3 pumice, 7% sodium dodecyl sulfate, 6% glyceryl stearate, 5% polysorbate 20, 5% cetyl alcohol, 1% silicone, and 0.5% benzyl alcohol, made up as a paste in water.

Example 7

The granular composition is prepared consisting of, by weight, 26% no. 3 pumice, 7% sodium dodecyl sulfate, 6% glyceryl stearate, 5% polysorbate 20, 4% candelilla, 1% silicone, and 0.5% benzyl alcohol, made up as a paste in water.

Example 8

The granular composition is prepared consisting of, by weight, 20% no. 4 pumice, 7% sodium dodecyl sulfate, 6% glyceryl stearate, 5% polysorbate 20, 5% cetyl alcohol, 1% beeswax, 1% silicone, and 0.5% benzyl alcohol, made up as a paste in water.

Example 9

The granular composition is prepared consisting of, by weight, 30% no. 3 pumice, 9% sodium dodecyl sulfate, 5% glyceryl stearate, 4% polysorbate 20, 5% cetyl alcohol, 1% silicone, and 1% Germaben II, made up as a paste in water.

Example 10

The granular composition is prepared consisting of, by weight, 30% coarse olivine sand, 7% sodium dodecyl sulfate, 6% glyceryl stearate, 5% polysorbate 20, 3% paraffin wax, 1% silicone, and 1% Germaben II, made up as a thick paste in water, Example 11

The granular composition is prepared consisting of, by weight, 12% no. 3 pumice, 7% sodium dodecyl sulfate, 5% glyceryl stearate, 4% polysorbate 20, 3% paraffin wax, 1% silicone, and 1% Germaben II, made up as a paste in water.

Example 12

The granular composition is prepared consisting of, by weight, 18% no. 3 pumice, 4% no. 4 pumice, 6% sodium myristyl sulfate, 5% glyceryl stearate, 5% polysorbate 80, 2% paraffin wax, and 1% Germaben II, made up as a paste in water.

The entire disclosures of all applications, patents and publications cited above and below are hereby incorporated by reference.

It will be appreciated by those skilled in the art that variations can be made in the particular method of use, which will depend on a variety of factors, all of which are considered routinely when treating individuals. It will also be understood, however, that the specific treatment for any given patient will depend upon a variety of factors, including, but not limited to the particular composition employed, the age of the patient, the general health of the patient, the gender of the patient, the diet of the patient, time of administration, and the medical history of the patient. It will be further appreciated by one skilled in the art that the optimal course of treatment, i.e., the mode of treatment and the daily number of treatments, can be ascertained by those skilled in the art using conventional treatment tests. The invention may be embodied in other specific forms without departing from the spirit or essential characteristics thereof. The foregoing examples are included by way of illustration only. Accordingly, the scope of the invention is limited only by the scope of the appended claims.

What is claimed is:

1. A method of treating photoaging of skin comprising:
   applying a granular composition to an exterior surface of the skin,
   the method further comprising rolling said granular composition on said surface of said skin with at least one of a circular, longitudinal, and reciprocating motion, wherein said granular composition comprises between about 12% (w/w) and about 30% (w/w) coarse, water-insoluble particles of a size of about 0.3 mm or greater having a hardness on the Moh scale of about 3 to about 7 in an aqueous emulsion,
   with the proviso that the emulsion does not comprise soap, whereby thickness of the skin is increased.

2. The method of claim 1 further comprising applying said granular composition to said skin daily.

3. The method of claim 1 wherein said particle is pumice.

4. The method of claim 3 wherein said pumice is characterized as having a particle size of about 0.3 mm.

5. The method of claim 1 wherein said skin is facial skin.

6. The method of claim 1 wherein said skin is hand skin.

7. The method of claim 1 wherein said skin is selected from at least one of shoulder, chest, back, scalp, and arm skin.

8. The method of claim 1 wherein the granular composition further comprises between about 2% (w/w) and about 8% (w/w) of at least one wax.

9. The method of claim 8 wherein the wax is cetyl alcohol.

* * * * *